US00PP16649P2

(12) United States Plant Patent
Trees

(10) Patent No.: US PP16,649 P2
(45) Date of Patent: Jun. 13, 2006

(54) ***GAILLARDIA* PLANT NAMED 'BALTOREDEM'**

(50) Latin Name: *Gaillardia pulchella*
Varietal Denomination: Baltoredem

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 87 days.

(21) Appl. No.: 11/016,179

(22) Filed: Dec. 17, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Gaillardia* plant named 'Baltoredem', characterized by its red/yellow bicolor flowers, freely branching character, and vigorous, upright, and mounded growth habit.

2 Drawing Sheets

Latin name of genus and species of plant claimed: *Gaillardia pulchella.*
Variety denomination: 'Baltoredem'.

BACKGROUND OF THE INVENTION

The present invention relates to a new and distinct cultivar of *Gaillardia* plant botanically known as *Gaillardia pulchella* and hereinafter referred to by the cultivar name 'Baltoredem'.

The new cultivar originated as the product of the open field pollination of the *Gaillardia* cultivar 'Baltorflam', U.S. Plant patent application Ser. No. 10/741,570. The new *Gaillardia* was discovered and selected as a single flowering plant within the progeny of the above stated open-pollination during February 2000 at Arryo Grande, Calif.

Asexual reproduction of the new cultivar by terminal stem cuttings since February 2000 at Arroyo Grande, Calif. and West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Baltoredem' as a new and distinct cultivar of *Gaillardia* plant:

1. Red/yellow bicolor flowers.
2. Upright and mounded plant habit.
3. Freely branching character.
4. Vigorous growth habit.

Plants of the new cultivar differ from the female parent, 'Baltorflam', primarily in flower color. Plants of the new cultivar may also be compared to the commercially grown *Gaillardia* cultivar Baltorslam, however plants of the new cultivar have larger ray florets and different ray floret color than plants of the cultivar Baltorslam.

BRIEF DESCRIPTION OF THE PHOTOGRAPHS

The accompanying photographs show, as nearly true as it is reasonably possible to make the same in color illustrations of this type, typical flower and foliage characteristics of the new cultivar. The plants were grown for 12 weeks in a greenhouse at West Chicago, Ill.

DETAILED BOTANICAL DESCRIPTION

Figure 1:
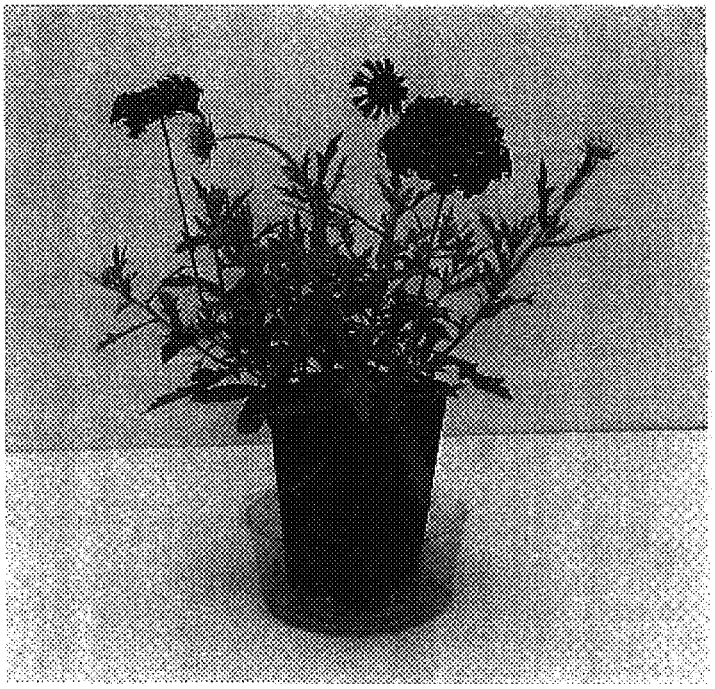
FIG. 1 illustrates the overall growth and flowering habit of 'Baltoredem'.
Figure 2:
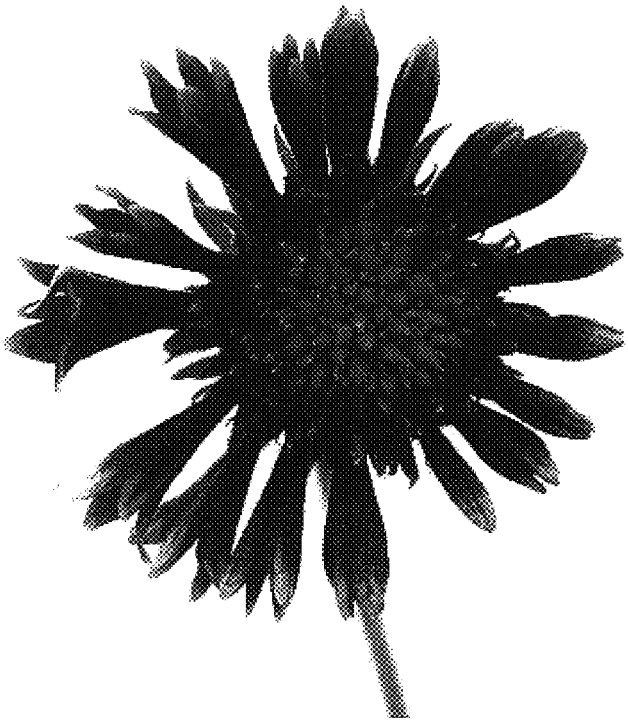
FIG. 2 illustrates a close-up view of an individual flower of 'Baltoredem' just beginning to open.
Figure 3:
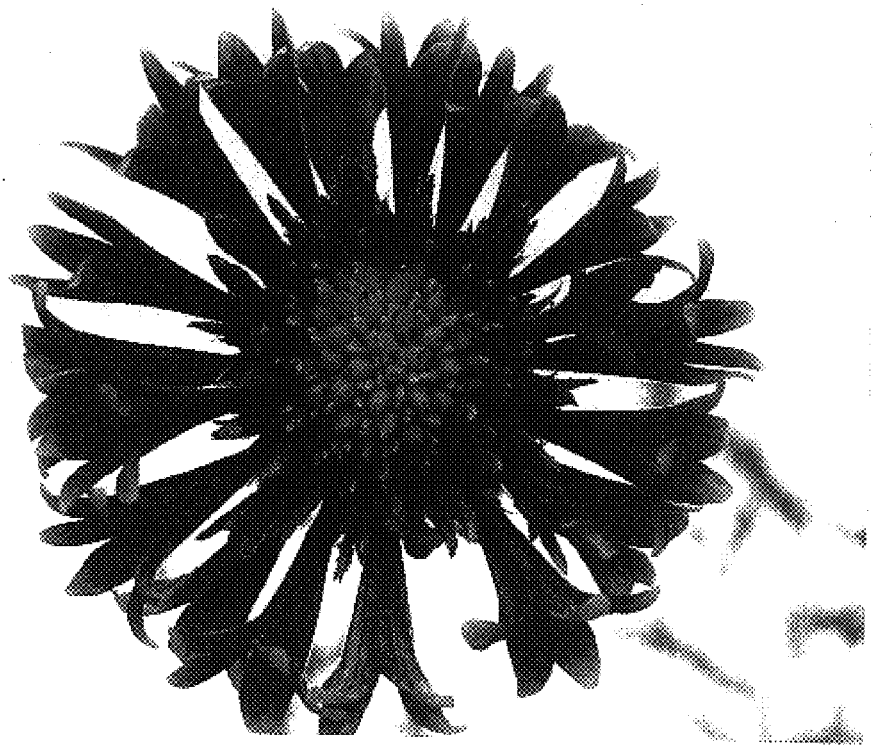
FIG. 3 illustrates a close-up view of an individual flower of 'Baltordeum' with all the ray florets open.
Figure 4:
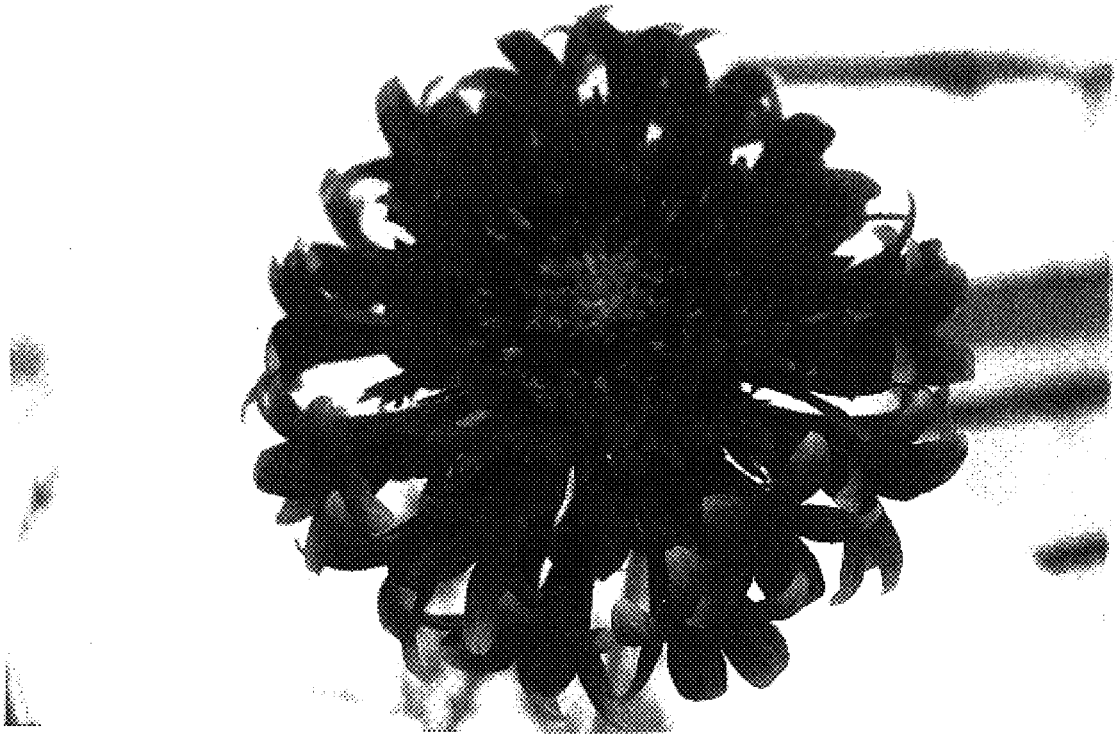
FIG. 4 illustrates a close-up view of an individual flower of 'Baltordeum' with all the ray florets and most of the disc florets open.

The new cultivar has not been observed under all possible environmental conditions to date. Accordingly, it is possible that the phenotype may vary somewhat with variations in the environment such as temperature, light intensity, and day length without, however, any variation in genotype.

The chart used in the identification of colors described herein is The R.H.S. Colour Chart of The Royal Horticultural Society, London, England 2001 edition, except where general terms of ordinary significance are used. The color values were determined on Sep. 27, 2004 in West Chicago, Ill. The readings were taken between 10:00 and 11:45 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. for 12 weeks in 10 cm pots while utilizing a soilless growth medium. Greenhouse temperatures were maintained at approximately 65°–75° F. (18°–24° C.) during the day and approximately 60° 65° F. (15° 18° C.) during the night. Greenhouse light levels of 5,000–8,000 footcandles were maintained during the day. Plants were pinched at three weeks after plantings.

Botanical classification: *Gaillardia pulchella* cultivar Baltoredem.

Parentage: Open-pollination of the *Gaillardia pulchella* cultivar Baltorflam, U.S. Plant patent application Ser. No. 10/741,570.

Propagation:

*Type cutting.*—Terminal stem.

*Time to initiate roots.*—Approximately 5 to 8 days.

*Time to develop roots.*—Approximately 21 to 28 days.

*Root description.*—Fibrous and well branched.

Plant description:

*General appearance and form.*—Upright, mounded and vigorous.

*Crop time.*—Approximately 6–7 weeks from planting rooted cuttings.

*Height from soil level to top of blooms.*—Approximately 38.6 cm.

*Diameter* (*area of spread*).—Approximately 46 cm.

*Branching habit.*—Freely basal branching.

*Branch description.*—Shape: Cylindrical. Quantity per plant: Approximately 3. Length: Approximately 25.1 cm. Diameter: Approximately 4 mm. Color: 144B. Texture: Strigose. Internode length: Approximately 2.2 mm.

*Foliage.*—Type: Simple. Arrangement: Alternate. Shape: Oblanceolate. Margin: Entire. Apex: Acute. Base: Attenuate. Venation pattern: Reticulate. Length of mature leaves: Approximately 4.2 cm. Width of mature leaves: Approximately 1 cm. Texture of upper and lower surface: Densely pubescent. Color of upper surface of mature foliage: Closest to 137B with veins of 144D. Color of lower surface of mature foliage: Closest to 137C with veins of 144D.

Flowering description:

*Outdoor flowering habit.*—'Baltoredem' is freely flowering under outdoor growing conditions with substantially continuous blooming from spring through autumn and year round in greenhouse environment.

*Inflorescence description.*—Solitary. Type: Composite. Appearance: Fully double, arising from leaf axils on strong peduncles. Aspect: Facing upward or outward. Quantity per plant: 3 open at any one time. Diameter: Approximately 5.3 cm. Depth: Approximately 3.2 cm. Disc diameter: Approximately 1.2 cm. Disc and ray florets arranged acropetally on a capitulum.

*Flower bud.*—Shape: Round. Diameter before color: Approximately 0.74 cm. Depth before color: 0.94 cm. Diameter at first color color: Approximately 1.7 mm. Depth at first color: 1 cm. Texture: Pubescent. Color: 145A in center, 150C at margin.

*Ray florets.*—Quantity: Approximately 77 per Inflorescence. Arrangement: Radiate. Shape: Elongated, cupped. Formed by 5 petals fused at base. Length: Approximately 2.9 cm. Length of petals from throat to apex: Approximately 9 mm. Width at apex: Approximately 1.3 cm. Apex: Acute. Base: Attenuate. Margin: Entire. Texture of upper surface: Glabrous. Texture of lower surface: Glabrous with slight pubescence at base where petals fuse. Color: Fully opened, upper surface: 13A at apex transitioning through 24A and N 34A in center of petal to 59B where petals fuse. Fully opened, lower surface: 13C at apex with 59B at base where petals fuse.

*Disc florets.*—Quantity: Approximately 71. Shape: Cylindrical with 7 acuminate lobes at apex. Length: Approximately 8 mm. Diameter: Approximately 1.3 mm. Texture: Glabrous. Color: 53A at apex, 53B in center, and 54D at base.

*Receptical.*—Shape: Cone. Diameter: Approximately 1.2 cm. Depth: Approximately 6 mm. Color: Slightly lighter than 145A.

*Peduncle.*—Strong, erect. Length: Approximately 5.5 cm. Diameter: Approximately 2 mm. Texture: Strigose. Color: Closest to 145A.

*Involucral bracts.*—Quantity: Approximately 29. Shape: Lanceolate. Apex: Acuminate. Base: Truncate. Margin: Entire. Length: Approximately 9 mm. Width: Approximately 3 mm at base. Texture: Moderate to dense.

*Reproductive organs.*—Androecium — On disc florets. Stamen number: 5. Filaments: Adanate to corolla. Anther shape: Linear, fused around style. Anther length: Approximately 2.6 mm. Anther color: N167B. Amount of pollen: Abundant. Pollen color: 21A. Gynoecium — On disc and ray florets. Pistil quantity: 1 per floret. Pistil length: Approximately 1.9 cm. Stigma shape: 2 parted. Stigma length: Approximately 4 mm. Stigma color: 187A. Style length: 5 mm. Style color: N155B. Ovary length: 1 mm. Ovary color: 145C.

Seed and fruit production: Neither seed nor fruit production has been observed.

Disease and pest resistance: Resistance to pathogens or pests common to *Gaillardia* has not been observed.

What is claimed is:

1. A new and distinct cultivar of *Gaillardia* plant named 'Baltoredem', substantially as herein shown and described.

* * * * *